United States Patent [19]

Forbus et al.

[11] Patent Number: 4,504,690

[45] Date of Patent: Mar. 12, 1985

[54] ORGANOPHOSPHORUS-TREATED ZEOLITE CATALYSTS FOR PARA-SELECTIVE AROMATICS CONVERSION

[75] Inventors: Nancy P. Forbus, Newtown, Pa.; Warren W. Kaeding, Lawrenceville, N.J.

[73] Assignee: Mobil Oil Corporation, New York, N.Y.

[21] Appl. No.: 614,195

[22] Filed: May 25, 1984

Related U.S. Application Data

[60] Division of Ser. No. 489,424, Apr. 28, 1983, Pat. No. 4,469,806, which is a continuation-in-part of Ser. No. 359,560, Mar. 18, 1982, Pat. No. 4,409,132.

[51] Int. Cl.³ .............................................. C07C 2/68
[52] U.S. Cl. ...................................... 585/466; 585/467
[58] Field of Search ................................ 585/466, 467

[56] References Cited

U.S. PATENT DOCUMENTS

| 3,962,364 | 6/1976 | Young | 585/466 |
|---|---|---|---|
| 4,044,065 | 8/1977 | Butter et al. | 585/409 |
| 4,117,024 | 9/1978 | Kaeding | 585/466 |
| 4,117,026 | 9/1978 | Haag et al. | 585/467 |
| 4,137,195 | 1/1979 | Chu | 502/77 |
| 4,329,533 | 5/1982 | Chu | 585/467 |
| 4,356,338 | 10/1982 | Young | 585/407 |
| 4,423,266 | 12/1983 | Young | 585/466 |
| 4,433,187 | 2/1984 | Young | 585/466 |
| 4,444,989 | 4/1984 | Herkes | 585/467 |

*Primary Examiner*—Delbert E. Gantz
*Assistant Examiner*—Cynthia A. Prezlock
*Attorney, Agent, or Firm*—A. J. McKillop; J. F. Powers, Jr.; Edward F. Kenehan, Jr.

[57] ABSTRACT

A method is provided for treating modified ZSM-5 type zeolite catalysts with a vapor phase organophosphorus reagent such as trimethylphosphite or dimethylmethylphosphonate in order to improve the para-selective properties of such catalysts for the conversion of aromatic materials. The modified zeolites so treated are those which contain a minor proportion of a difficultly reducible oxide such as magnesium oxide, calcium oxide and/or phosphorus oxide. Such catalyst compositions can be used in alkylation, transalkylation or disproportionation processes to provide alkylated aromatic product mixtures having exceptionally high concentrations of the para-dialkylbenzene isomer.

8 Claims, No Drawings

ORGANOPHOSPHORUS-TREATED ZEOLITE CATALYSTS FOR PARA-SELECTIVE AROMATICS CONVERSION

CROSS-REFERENCE TO RELATED APPLICATIONS

This application is a division of copending U.S. application Ser. No. 489,424, filed April 28, 1983 now U.S. Pat. No. 4,469,806, which is a continution-in-part of U.S. application Ser. No. 359,560, filed Mar. 18, 1982, now U.S. Pat. No. 4,409,132. The entire disclosures of these applications and patents are expressly incorporated herein by reference.

BACKGROUND

The present invention relates to the preparation and use of modified zeolite catalyst compositions which are especially suitable for the conversion of aromatic hydrocarbons to provide product mixtures enriched in the para-(or 1,4-) dialkyl substituted benzene isomer.

Production of dialkyl substituted benzene compounds via alkylation, transalkylation or disproportionation of aromatic hydrocarbons is an important step in a number of commercial chemical manufacturing processes. Such reactions can be carried out over a variety of catalyst materials. Alkylation of aromatic hydrocarbons utilizing crystalline aluminosilicate catalysts has, for example, been described. U.S. Pat. No. 2,904,697 to Mattox refers to alkylation of aromatic hydrocarbons with an olefin in the presence of a crystalline metallic aluminosilicate having uniform openings of about 6 to 15 Angstrom units. U.S. Pat. No. 3,251,897 to Wise describes alkylation of aromatic hydrocarbons in the presence of X or Y-type crystalline aluminosilicate zeolites, specifically such type zeolites wherein the cation is rare earth and/or hydrogen. U.S..Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The disproportionation of aromatic hydrocarbons in the presence of zeolite catalysts has been described by Grandio et al in the *Oil and Gas Journal*, Vol. 69, No. 48 (1971), U.S. Pat. Nos. 3,126,422; 3,413,374, 3,598,878; 3,598,879 and 3,607,961 show vapor-phase disproportionation of toluene over various catalysts.

In many of these prior art processes, the dialkylbenzene product produced frequently contains more of the 1,3 isomer than of the other two isomers. For example, xylene produced via the conventional catalytic methylation of toluene can have the equilibrium composition of approximately 24 percent of 1,4-, 54 percent of 1,3- and 22 percent of 1,2- isomer. Of the dialkylbenzene isomers, 1,3-dialkylbenzene is often the least desired product, with 1,2- and 1,4-dialkylbenzene being the more useful products. 1,4-Dimethylbenzene, for example, is of particular value, being useful in the manufacture of terephthalic acid which is an intermediate in the manufacture of synthetic fibers such as "Dacron". Furthermore, 1,4- methylethylbenzene, i.e., para-ethyltoluene (PET), is useful for subsequent conversion to para-methylstyrene, and for this purpose ethyltoluene products containing as much as 97% of the para isomer can be required.

Mixtures of dialkylbenzene isomers, either alone or in further admixture with ethylbenzene, have previously been separated by expensive superfractionation and multistage refrigeration steps. Such processes, as will be realized, involve high operation costs and have a limited yield. Alternatively, various modified zeolite catalysts have been developed to alkylate toluene with a greater or lesser degree of selectivity to 1,4-dialkylbenzene isomers. Hence, U.S. Pat. Nos. 3,972,832, 4,034,053, 4,128,592, and 4,137,195 disclose particular zeolite catalysts which have been treated with compounds of phosphorus and/or magnesium to increase para-selectivity of the catalysts. Para-selective boron-containing zeolites are shown in U.S. Pat. No. 4,067,920 and para-selective, antimony-containing zeolites in U.S. Pat. No. 3,979,472. Similarly, U.S. Patent Nos. 3,965,208; 4,117,026; 4,259,537; 4,260,843; 4,275,256; 4,276,437; 4,276,438; 4,278,827 and 4,288,647 all disclose other zeolites modified with various oxides to improve catalyst para-selectivity.

Even though catalyst treatment procedures have been developed to render zeolite catalysts highly para-selective for aromatics conversion, aromatics conversion processes employing such catalysts, and especially such processes conducted on a commercial scale, generally tend to have a deselectivating effect on the catalyst. Contaminants such as moisture, metals and/or halogen introduced into the catalyst bed with the feed or with diluents can markedly lower catalyst para-selectivity. Water formed in the catalyst bed as a reaction product of the hydrocarbon conversion reactions which occur therein (e.g. when a methanol reactant is employed) can also adversely affect catalyst para-selectivity. There is thus a continuing need to develop not only aromatic conversion catalysts which have high initial para-selectivity, but also catalyst treatment procedures which are useful for restoring diminished catalyst para-selectivity and reducing catalyst susceptibility to subsequent deselectivation.

Accordingly, it is an object of the present invention to provide methods for treating para-selective zeolite-based aromatics conversion catalysts to enhance their initial or subsequently diminished para-selectivity characteristics or to reduce catalyst susceptibility to subsequent deselectivation.

It is a further object of the present invention to provide modified zeolite catalyst compositions which effectively promote the conversion of aromatics to produce mixtures containing an exceptionally high percentage, e.g., 80% by weight or more for alkylation of toluene, of para-dialkylbenzene isomer.

It is a further object of the present invention to provide highly para-selective aromatics conversion processes employing the modified zeolite catalysts described herein.

SUMMARY

The present invention provides a method for treating modified zeolite catalysts to render such catalysts highly para-selective and resistant to deselectivation by water or halogen contaminants when used for the conversion of aromatic compounds to produce dialkyl substituted benzene compounds. The zeolite component of the catalysts so treated is one which has a silica to alumina mole ratio of at least 12 and a constraint index within the approximate range of 1 to 12. Such zeolite catalysts are further modified by incorporation thereinto of a minor proportion of a difficultly reducible oxide.

In accordance with the present invention, such catalysts are contacted with an organophosphorus reagent in the vapor phase at a temperature between about 100° C. and 300° C. for a period of time and under conditions sufficient to either enhance catalyst para-selectivity or reduce catalyst susceptibility to deselectivation by contact with moisture or halogen. The organophosphorus reagents employed in such treatment can be the $C_{1-4}$ alkylphosphite esters, the $C_{1-4}$ alkylphosphate esters, or dimethylmethylphosphonate.

The present invention also relates to modified catalyst compositions treated in this manner and to alkylation, transalkylation and disproportionation processes utilizing such treated modified catalyst compositions.

DETAILED DESCRIPTION

The catalysts which are treated in accordance with the method of the present invention are zeolite based catalysts which promote the conversion of aromatic compounds. One essential component of such catalysts is a particular type of crystalline zeolite material which exhibits unusual properties. Although these zeolites have unusually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 70 and above, 200 and above or even 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Thus also to be included within the zeolite definition are substantially pure silica forms of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Catalyst-56 | 1.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The descriptions contained within those patents include the X-ray diffraction pattern of therein disclosed ZSM-5.

ZSM-11 is described in U.S. Pat. No. 3,709,979. The description in that patent includes the X-ray diffraction pattern of said ZSM-11.

ZSM-12 is described in U.S. Pat. No. 3,832,449. The description in that patent includes the X-ray diffraction pattern for ZSM-12.

ZSM-23 is described in U.S. Pat. No. 4,076,842 along with a specification of the X-ray diffraction pattern of the disclosed ZSM-23 zeolite.

ZSM-35 is described in U.S. Pat. No. 4,016,245 along with a description of the X-ray diffraction pattern of the zeolite.

ZSM-38 is more particularly described in U.S. Pat. No. 4,046,859. The description of that zeolite in that patent includes the X-ray diffraction pattern of ZSM-38.

ZSM-48 is more particularly described in U.S. Pat. No. 4,375,573. Such a description includes the X-ray diffraction pattern for ZSM-48.

It is to be understood that by incorporating by reference the foregoing patent documents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patent documents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite can be employed as precursors to the oxide-modified zeolites of the present invention. Such other forms of the zeolite are those wherein the original alkali metal content has been reduced to less than about 50 percent by weight of the original alkali metal contained in the zeolite as synthesized, usually 0.5 percent by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing aromatics conversion processes using the treated catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

A second essential component of the aromatics conversion catalysts treated in accordance with the present invention comprises a minor proportion, e.g., from about 0.05% to 50% by weight of the catalyst composite, of a difficultly reducible oxide, incorporated into the zeolite. Oxides of this type can include oxides of phosphorus as well as those oxides of the metals of Groups IA, IIA, IIIA, IVA, VA, VIA, VIIA, VIIIA, IB, IIB, IIIB, IVB, or VB of the Periodic Chart of the Elements (Fisher Scientic Company, Catalog No. 5-702-10) which serve to enhance the para-selectivity properties of the catalysts modified therewith. The difficultly reducible oxides most commonly employed to modify the selectivity properties of the zeolite-based catalysts herein are oxides of phosphorus and magnesium. Thus, the catalysts herein can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such catalysts at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3–5 hours but may be extended to 24 hours or longer.

As discussed more fully hereinafter, the optional incorporation of phosphorus into the zeolite composite as one of the useful difficultly reducible oxides is a catalyst treatment procedure distinct from the subsequent essential catalyst treatment step of the present invention which involves contact of the catalyst composite with particular vapor phase organophosphorus reagents under particular reaction conditions. It is thus possible for a catalyst composite to be modified in accordance with the present invention by two separate treatments with phosphorus compounds, the first of such treatments serving to incorporate an oxide of phosphorus as all or part of the difficultly reducible oxide component and the second such treatment serving to provide the additional catalyst para-selectivity benefits of the present invention.

Magnesium oxide is another preferred difficultly reducible oxide which can be incorporated with the zeolite composites in a manner similar to that employed with phosphorus. Magnesium can comprise from about 0.25% to 25% by weight preferably from about 1% to 15% by weight present at least in part as magnesium oxide. As with phosphorus, magnesium oxide incorporation is effected by contacting the zeolite composite with an appropriate magnesium compound followed by drying and calcining to convert magnesium in the zeolite to its oxide form. Preferred magnesium-containing compounds include magnesium nitrate and magnesium acetate. Calcination times and temperatures are generally the same as recited hereinabove for calcination of phosphorus-containing catalysts.

In addition to treatment of the zeolite composites to incorporate phosphorus and/or magnesium oxides as hereinbefore described in detail, such zeolites may also be modified in a substantially similar manner to incorporate thereinto a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Ser. No. 139,611, filed Apr. 11, 1980); iron and/or cobalt (U.S. Ser. No. 150,868, filed May 19, 1980); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

Treatment of the zeolite catalysts to incorporate any of the foregoing oxide materials to enhance para-selectivity will generally occur before such catalysts are treated with organophosphorus materials in accordance with the present invention in order to provide even greater enhancement and/or restoration of the para-selective properties of such catalysts. Additional catalyst modifying procedures which may also optionally be employed to modify catalyst activity or selectivity include precoking and presteaming (i.e., before oxide incorporation), or combinations thereof.

In accordance with the present invention, the oxide-modified, para-selective, zeolite-based catalyst composites as hereinbefore described are treated with an organophosphorus reagent under particular conditions to enhance catalyst aromatics conversion para-selectivity, i.e., to either restore diminished para-selectivity or improve inherent para-selectivity, or to reduce the susceptibility of the catalyst to deselectivation by contact with moisture. The organophosphorus reagents utilized in the present invention are particular materials selected from the wide variety of phosphorus compounds which have heretofore been used to modify aromatics conversion catalysts to enhance para-selectivity. It has now been suprisingly discovered that only certain of such phosphorus compounds can be usefully employed in the context of the present invention to selectivate, reselectivate or reduce susceptibility to moisture or halogen, e.g., chloride, deselectivation of the zeolite catalysts herein whereas others of such phosphorus materials are not effective in bringing about such para-selectivity-related improvements.

The particular organophosphorus reagents employed in the present invention are selected from $C_1$ to $C_4$ alkyl phosphite esters, $C_1$ to $C_4$ alkyl phosphate esters and dimethylmethylphosphonate. The phosphite and phosphate esters include those having the formulas $(R_1O)(R_2O)(R_3O)P$ and $(R_1O)(R_2O)(R_3O)P=O$ wherein $R_1$, $R_2$ and $R_3$ are each lower alkyl of 1 to 4 carbon atoms. Examples of such organophosphous reagents include trimethylphosphite, tributylphosphite, trimethylphosphate and tributylphosphate. Dimethylmethylphosphonate has the general formula $CH_3P(O)(OCH_3)_2$ and is the trimethyl derivative of phosphonic acid. The preferred organophosphorus reagents are trimethylphosphite and dimethylmethylphosphonate.

Catalyst contact with the organophosphorus reagent occurs with the organophosphorus material in the vapor phase and under conditions which either enhance catalyst para-selectivity or reduce catalyst deselectivation susceptibility. Such conditions generally include a contact temperature of from about 100° C. to 300° C., more preferably from about 150° C. to 300° C. Such conditions can also include an organophosphorus reagent/catalyst contact time of from about 0.1 to 2 hours, preferably from about 0.2 to 0.8 hours. The amount of organophosphorus reagent employed is not critical so long as reagent contact with the catalyst is sufficient to enhance the para-selectivity or reduce the deselectivation susceptibility of the treated catalyst with respect to its utility in promoting conversion of aromatics to dialkyl substituted benzene compounds. Thus, generally catalyst can be contacted with at least about 0.5 gram of organophosphorus reagent per gram of catalyst per hour, more preferably with at least about 2 grams of organophosphorus reagent per gram of catalyst per hour.

Organophosphorus reagent used to treat the specified catalysts of the present invention can be admixed with an inert inorganic gaseous diluent. Inert diluent carriers of this type include nitrogen, carbon dioxide, helium and the like. During contact with the modified catalyst, the organophosphorus treating agent mixture should be maintained substantially free of organic diluents such as methanol.

After treatment with organophosphorus reagent, the modified catalysts of the present invention may optionally again be calcined in conventional manner to render the catalyst more suitable for use in promoting aromatics conversion reactions. Thus, after organophosphorus treatment is completed to the extent desired, the treated modified catalyst can be contacted with an atmosphere maintained at a temperature from about 100° C. to 1000° C. for a period of from about 1 to 72 hours. Calcination is generally conducted in a suitable oxygen-containing atmosphere, e.g. air, which may also contain diluents such as nitrogen, helium and the like.

It has been surprisingly discovered that treatment of the particular modified zeolite catalyst composites of this invention with organophosphorus reagent in the manner herein described can provide one or more benefits with respect to catalyst para-selectivity when such catalysts are used to promote the conversion of aromatic compounds to dialkyl substituted benzene compounds. In some instances, treatment of oxide-modified zeolite catalysts with the particular organophosphorus materials described herein in accordance with the present invention will provide enhancement of the para-selective characteristics of the catalyst even though the catalyst may already be highly para-selective by virtue of the incorporation therein of the requisite difficultly reducible oxide, for example, magnesium, calcium and/or even phosphorus. In other instances, treatment of the catalysts herein with the organophosphorus materials of the present invention can bring about reselectivation of damaged para-selective catalysts which have had their para-selectivity characteristics diminished by contact with moisture or contaminants such as metals or halogens in the course of hydrocarbon conversion operations. Finally, it has been discovered that organophosphorus treatment of either damaged or undamaged oxide-modified catalysts in accordance with the present invention can reduce the susceptibility of such catalysts to deselectivation by moisture or halogen, e.g., chloride, contaminants, in the course of subsequent aromatics conversion operations.

The treated zeolite catalysts of the present invention are advantageously used to promote conversion of aromatic compounds to provide dialkyl substituted benzene product mixtures which are highly enriched in the para-dialkyl substituted benzene isomer. Conversion reactions of this type thus include aromatics alkylation, transalkylation and disproportionation.

Alkylation of aromatic compounds in the presence of the above-described catalysts can be effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5$ $N/M^2$ to $10^7$ $N/m^2$ (1–100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzene, diethylbenzene, methylethylbenzene, propylbenzene, isopropylbenzene, isopropylmethylbenzene, or substantially any mono- or di-substituted benzenes which are alkylatable in the 4-position of the aromatic ring.

The molar ratio of alkylating agent to aromatic compound is generally between about 0.05 and about 2. For instance, when methanol is employed as the methylating agent and toluene is the aromatic, a suitable molar ratio of methanol to toluene has been found to be approximately 0.1 to 1.0 mole of methanol per mole of toluene. When ethylene is employed as the alkylating agent and toluene is the aromatic, a suitable molar ratio of ethylene to toluene is approximately 0.05 to 2.5 moles of ethylene per mole of toluene.

Alkylation is suitably accomplished utilizing a feed weight hourly space velocity (WHSV) of between about 1 and about 100, and preferably between about 1 and about 50. The reaction product, consisting predominantly of the 1,4-dialkyl isomer, e.g. 1,4-dimethylbenzene, 1-ethyl-4-methylbenzene, etc., or a mixture of the 1,4- and 1,3- isomers together with comparatively smaller amounts of 1,2-dialkylbenzene isomer, may be separated by any suitable means. Such means may include, for example, passing the reaction product stream through a water condenser and subsequently passing the organic phase through a column in which chromatographic separation of the aromatic isomers is accomplished.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene, and so forth.

Another process embodiment of this invention relates to the selective disproportionation of alkylated aromatic compounds to produce dialkylbenzenes wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example when toluene serves as the donor and acceptor of a transferred methyl group to produce benzene and xylene.

The transalkylation and disproportionation reactions are carried out by contacting the reactants with the above described treated modified zeolite catalyst at a temperature of between about 250° C. and 750° C. at a pressure of between atmospheric ($10^5$ $N/m^2$) and about 100 atmospheres ($10^7$ $N/m^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any mono-substituted alkylbenzene. These aromatic compounds are selectively converted to, respectively, 1,4-dimethylbenzene, 1,4-diethylbenzene, 1,4-dipropylbenzene, or other 1,4-dialkylbenzene, as appropriate, with benzene being a primary side product in each instance. The product is recovered from the reactor effluent by conventional means, such as distillation, to remove the desired products of benzene and dialkylbenzene, and any unreacted aromatic component is recycled for further reaction.

The aromatics conversion processes described herein may be carried out as batch type, semi-continuous or continuous operations utilizing a fixed or moving bed catalyst system. The catalyst after use in a moving bed reactor can be conducted to a regeneration zone wherein coke is burned from the catalyst in an oxygen-containing atmosphere, e.g. air, at an elevated temperature, after which the regenerated catalyst can be recycled to the conversion zone for further contact with the charge stock. In a fixed bed reactor, regeneration can be carried out in a conventional manner where an inert gas containing a small amount of oxygen (0.5–2%) is used to burn the coke in a controlled manner so as to limit the temperature to a maximum of around 500°–550° C.

The following examples will serve to illustrate certain specific embodiments of the hereindisclosed invention. These examples should not, however, be construed as limiting the scope of the invention, as there are many variations which may be made thereon without departing from the spirit of the disclosed invention, as those of skill in the art will recognize.

EXAMPLE I

Preparation of Mg-P-ZSM-5 Alkylation Catalyst

A typical Mg-and P-modified catalyst composition illustrating one type of catalyst used in evaluating the organophosphorus catalyst treatment procedure employed in this invention is described as follows. To prepare such a catalyst, $NH_4ZSM-5$ zeolite (9.75 kg.) having a crystal size of about 2 microns in the form of 1.6 mm (1/16 inch) diameter extrudate with a 35 weight percent alumina binder is used. The catalyst is pre-steamed at 593° C. for 2 hours at a gaseous steam rate of 2.83 l./min. The catalyst material is then impregnated with a solution of 3.9 kg. of diammonium acid phosphate in 16.2 l. of water and dried for about 16 hours in an open dish. The catalyst is then calcined in air at 500° C. for 3 hours to give a phosphorus-modified zeolite. The resulting product is cooled, and a portion (1.36 kg.) is impregnated with a solution of 3.4 kg. of magnesium acetate tetrahydrate in 2.7 l. of water, dried and calcined in air at 500° C. for 1 hour. The final catalyst contains 7.1 weight percent magnesium, present at least in part as the oxide, and 2.67 weight percent phosphorus, present at least in part as the oxide.

EXAMPLE II

Ethylation of Toluene Over Mg-P-ZSM-5 Catalyst

An Mg-P-ZSM-5 zeolite catalyst prepared in a manner substantially similar to that described in Example I is used to promote ethylation of toluene. In such a reaction, WHSVs of 3.4 for toluene and 0.5 for ethylene; a toluene to ethylene molar ratio of 2:1 and a temperature of 400° C. are employed. The toluene conversion in such a reaction is 26.2% (Theoretical conversion =50%), with the concentration of para-ethyltoluene in the ethyltoluene product being 81.2%.

The Mg-P-ZSM-5 catalyst is then treated with trimethylphosphite (TMP) in accordance with the method of the present invention. TMP along with an $N_2$ diluent is fed for 15 minutes into the catalyst at 250° C. The WHSV for TMP is 3.1 and for the $N_2$ co-feed is 2.9. Before and after such treatment, the catalyst is calcined for one hour at 500° C.

After treatment with TMP in this manner, the catalyst is then used to promote ethylation of toluene under the same conditions employed with the untreated catalyst. Toluene conversion using the TMP-treated catalyst is 19.7%. Selectivity to the para-ethyltoluene isomer is 100%. It can be seen from such experimentation that TMP treatment of the catalyst improves the para-selectivity of the Mg-P-ZSM-5 catalyst even though the catalyst has already been phosphorus-modified in conventional manner with diammonium acid phosphate.

EXAMPLE III

Preparation of Mg-ZSM-5 Alkylation Catalyst

A sample of $NH_4$ ZSM-5 having a crystallite size of approximately 2 microns, containing 35 percent alumina binder, in the form of 1.6 mm (1/16 inch) extrudate is treated for 1 hour with a 60 wt % solution of $Mg(NO_3)_2 \cdot 6H_2O$ in water. Thereafter the catalyst is filtered, dried and calcined in air to provide a catalyst composite which contains approximately 5% by weight of magnesium. Catalysts of this general type, in some cases damaged by exposure to water or contaminants, are used in subsequent exemplification herein to demonstrate the catalyst treatment process of the present invention.

EXAMPLE IV

Para-Selective Aromatics Conversion Over Damaged Mg-ZSM-5

A procedure was established to evaluate various test catalysts of the Example III type for their performance in promoting para-selective aromatic conversion reactions. In accordance with such a procedure, 2.2 grams of the test catalyst, 14–24 mesh, is centered in a quartz reactor. Low surface area quartz chips are used to position the catalyst and fill void spaces. After calcination with air at 500° C. for one hour, the temperature is adjusted to 425° C. Toluene is fed to the reactor at a rate of 8.8 cc/hr. with a WHSV of 3.5. A temperature rise occurs, and temperature is immediately adjusted to 450° C. After 25 minutes on stream at 450° C., a water condenser is used to collect the liquid product for a period of 5 minutes for analysis. A 2 cc gas sample is also taken at this time for analysis at a position just after the water condenser. The temperature is then increased rapidly and successively to 500° C., 550° C. and 600° C. In a similar manner, liquid and gaseous samples are taken for analysis at each temperature during the last five minutes of a 30-minute run. This series of tests is used to determine performance for selective toluene disproportionation to produce p-xylene and benzene.

The reactor is then purged with nitrogen (without regeneration) and the temperature adjusted to 375° C. Toluene is fed at a rate of 19.8 cc/hr, WHSV of 7.8, then ethylene is added at 15.6 cc/min., WHSV of 0.5, and the nitrogen purge is stopped. The temperature is rapidly adjusted to 400° C. In a similar manner, gaseous and liquid samples are taken during the last five minutes of a 30-minute run. An additional test run is made at 450° C. This series of tests is used to determine performance for the alkylation of toluene with ethylene to produce p-ethyltoluene.

The reactor is purged with nitrogen, and the temperature adjusted to 380° C. without regeneration. A 4/1 molar mixture of toluene/methanol at a rate of 29 cc/hr., WHSV=11, is fed to the reactor and the temperature immediately adjusted to 400° C. In a similar manner; samples of gas and liquid are taken during the last five minutes of each 30-minute run at 400° C., 500° C. and 600° C.

Using these catalyst evaluation procedures, a sample of a base catalyst as generally described in Example III was tested for its performance in the toluene disproportionation and alkylation reactions described. Such a catalyst had been previously employed in a pilot plant operation to promote ethylation of toluene and had been damaged by exposure to moisture in the toluene feed. Results are provided in Table I.

TABLE I

Para-Selectivity of Damaged Mg—ZSM-5 Base Catalyst

| REACTION | SELECTIVITY TO PARAISOMER (% by weight) | CONVERSION RANGE (% by weight) |
|---|---|---|
| Toluene Disproportionation | | 1.2–17.3 |
| 450° C. | 67.8 | |
| 500° C. | 65.4 | |
| 550° C. | 58.4 | |
| 600° C. | 52.6 | |
| Toluene Alkylation w/Ethylene | | 9.3–13.9 |
| 400° C. | 88.3 | |
| 450° C. | 84.5 | |
| Toluene Alkylation w/Methanol | | 8.7–17.3 |
| 400° C. | 87.1 | |
| 500° C. | 73.5 | |
| 600° C. | 64.5 | |

The Table I data illustrate that the damaged Mg-ZSM-5 catalyst sample still exhibits some para-selectivity which, unlike conversion, decreases with increase in temperature.

EXAMPLE V

Para-Selective Aromatics Conversion over Organophosphorus-Treated Mg-ZSM-5

Samples of the damaged Mg-ZSM-5 catalyst of Example IV are treated with various organophosphorus reagents under various temperature conditions and then again tested for aromatics conversion activity and selectivity in accordance with the procedures of Example IV. In such testing, the damaged Mg-ZSM-5 which had been used in the base aromatics conversion testing of Example IV is calcined at 500° C. for one hour and then subjected to the organophosphorus treating agent for 15 minutes at the desired treatment temperature. Organophosphorus reagent is passed over the catalyst bed at the rate of 15 ml/hr; nitrogen is co-fed at a rate of approximately 60 cc/min. Following treatment, the catalyst sample is again calcined at 500° C. for one hour and then used in the aromatics conversion testing procedure hereinbefore described.

Results of such aromatics conversion testing for catalyst samples treated with trimethylphosphite $[P(OCH_3)_3]$, tributylphosphite $[P(OC_4H_9)_3]$, tributylphosphine $[P(C_4H_9)_3]$ and tributylphosphonate $[(C_4H_9O)_2(C_4H_9)P=O]$ are shown in Table II.

TABLE II

TREATED DAMAGED Mg—ZSM—5
(Para-Isomer in Primary Product, %, and Toluene Conversion, %)

| | TMP, 200° C. 15 min(a) | TMP, 500° C. 15 min | P(OBu)₃, 100° C. 15 min | P(OBu)₃, 300° C. 15 min | PBu₃ 100° C. | PBu₃ 300° C. | (BuO)₂BuP=O, 100° C. | (BuO)₂BuP=O, 500° C. |
|---|---|---|---|---|---|---|---|---|
| TOL DISPROPORT(b) | | | | | | | | |
| 450° C. | 88.9 | 70.4 | 72.1 | 92.7 | 70.8 | 63.9 | 65.6 | 41.8 |
| 500 | 92.5 | 69.4 | 71.1 | 93.8 | 65.9 | 56.8 | 60.4 | 40.6 |
| 550 | 93.5 | 64.4 | 67.8 | 92.4 | 60.7 | 53.7 | 58.4 | 44.1 |
| 600 | 92.0 | 73.9 | 63.4 | 91.1 | 56.2 | 49.9 | 55.6 | 47.3 |
| (Conv) | 0.9–7.0 | 0.7–1.6 | 1.5–15.5 | 1.0–11.3 | 1.1–16.1 | 1.7–18.5 | 1.5–17.9 | 1.7–4.1 |
| TOL + C₂H₄(c) | | | | | | | | |
| 400° C. | 98.8 | 100 | 91.2 | 98.4 | 88.6 | 85.2 | 88.7 | 75.1 |
| 450 | 98.5 | 100 | 89.0 | 98.1 | 85.9 | 81.8 | 86.9 | 74.4 |
| (Conv) | 6.9–8.9 | 0.8–0.9 | 7.7–9.9 | 6.2–7.5 | 7.0–10.1 | 7.4–11.0 | 6.6–9.4 | 1.9 |
| TOL + MeOH(d) | | | | | | | | |
| 400° C. | 97.9 | 55.1 | 90.9 | 94.5 | 88.9 | 88.2 | 54.0 | 64.4 |
| 500 | 97.2 | 65.3 | 85.3 | 90.9 | 80.6 | 81.3 | 50.1 | 59.2 |
| 600 | 92.6 | 72.1 | 65.1 | 60.2 | 69.4 | 70.7 | 62.8 | 57.5 |
| (Conv) | 6.3–10.4 | 7.0–17.0 | 9.3–19.5 | 1.9–6.6 | 10.7–20.2 | 10.0–20.0 | 0.6–1.0 | 1.5–2.0 |

(a)Reagent and catalyst treatment conditions.
(b)Selective toluene disproportionation.
(c)Alkylation of toluene with ethylene to produce p-ethyltoluene.
(d)Alkylation of toluene with methanol to product p-xylene.

A comparison of the aromatics conversion data from Tables I and II indicates that the trialkylphosphite treating agents of the present invention can, within the temperature ranges of the present invention, restore para-selectivity to the damaged Mg-ZSM-5 catalyst without undue loss of catalyst activity. Similar organophosphorus treating agents not within the scope of the present invention either do not significantly restore lost catalyst para-selectivity or do so at a significant loss of catalyst activity.

EXAMPLE VI

In this example, an Mg-ZSM-5 catalyst having para-selectivity diminished by generation of water during catalyst contact with methanol is treated several times with trimethylphosphite (TMP) and tested for its aromatics conversion performance in accordance with the general procedures of Example IV. In such TMP treatments, the catalyst sample is calcined at 500° C. for 1 hour and is then cooled to 155° C. TMP is metered into the catalyst bed at the rate of 20 ml/hr and mixed with nitrogen flowing at a rate of 100 cc/min. An exothermic reaction occurs to increase the temperature to about 190° C. in six minutes. The temperature is increased to 200° C. and maintained for about 15 minutes. The TMP feed is terminated, nitrogen flow is continued for about 5 minutes, and then air is introduced slowly as the temperature is increased to 550° C. over a period of about 30 minutes and maintained for a period of two hours in a flow of air at 100 cc/min.

A summary of the catalyst treatment procedures and the aromatic conversion screening results is provided in Table III.

| Analysis of Damaged PET Alkylation Catalyst | | | | |
|---|---|---|---|---|
| | Analysis, wt. % | | | |
| Reactor | Mg | Cl | Fe | Ni |
| Top | 8.61 | 0.89 | 0.34 | 0.02 |
| Bottom | 8.49 | 0.93 | 0.35 | 0.02 |

Subsequent investigation revealed that the toluene feed was contaminated with chlorinated hydrocarbons.

This contaminated catalyst was treated with gaseous trimethylphosphite in the manner described in Example VI. Catalyst was again tested for toluene disproportionation and ethylation in accordance with the procedures described in Example IV. Results are summarized in Table IV.

TABLE III

| Treatment of Mg—ZSM—5 Damaged by Water Generated During Methanol Conversion | | | | | | | | | |
|---|---|---|---|---|---|---|---|---|---|
| CATALYST | Mg—ZSM—5 | | P—Mg—ZSM—5 Gaseous TMP, Runs 1-9 *Pure MeOH Used Runs 10-12 | | P—Mg—ZSM—5 Calcine, 1 Hr 500° C., Air Runs 13-18 | | P—P—ZSM—5 Gaseous TMP 2nd Impreg. Runs 19-24 | | P—P—P—Mg—ZSM—5 Gaseous TMP 3rd Impreg. Runs 25-30 |
| TREATMENT | None | | | | | | | | |
| | Conv % | Para % | Conv % | Para % | Conv % | Para % | Conv % | Para % | Conv % | Para % |
| TOLUENE DISPROPORT. | | | | | | | | | | |
| 400° C. | 1.2 | 95.8 | 1.6 | 94.3 | 0.9 | 78.9 | 0.6 | 86.0 | 0.5 | 86.7 |
| 450 | 3.3 | 95.6 | 3.0 | 96.8 | 1.9 | 76.7 | 1.0 | 88.3 | 0.7 | 87.3 |
| 500 | 7.7 | 95.0 | 5.0 | 96.8 | 4.5 | 73.5 | 2.1 | 89.0 | 1.2 | 89.9 |
| 550 | 13.4 | 94.2 | 7.9 | 95.5 | 9.1 | 69.9 | 4.3 | 88.0 | 2.1 | 91.8 |
| TOL + $C_2H_4$ | | | | | | | | | | |
| 400° C. | 8.0 | 100 | 6.9 | 100 | 13.3 | 90.5 | 10.9 | 97.3 | 7.0 | 100 |
| 450 | 6.8 | 100 | 4.7 | 100 | 10.6 | 86.8 | 9.5 | 96.3 | 6.3 | 100 |
| TOL + MeOH | | | | | | | | | | |
| 400° C. | 6.4 | 98.4 | 2.2 | 68.3 | | | | | | |
| 500 | 9.3 | 96.2 | 4.3 | 87.5 | | | | | | |
| 600 | 8.5 | 94.5 | 5.6 | 65.1 | | | | | | |

*Results of Runs 10-12 wherein catalyst is contacted with pure methanol are not shown. Reaction of catalyst with methanol generates water in the catalyst bed which reduces catalyst selectivity. In subsequent runs, the methanol feed is not used and toluene methylation is not tested.

As the Table III data indicate, the initial screening shows high para-selectivity in all three types of toluene conversion for the catalyst sample. The initial treatment with TMP did not significantly increase para-selectivity for toluene disproportionation and ethylation since catalyst para-selectivity was already high initially. When methanol feed is used, water is generated in the catalyst bed and significantly reduces para-selectivity for all types of subsequent toluene conversion. Table III further indicates that this loss of catalyst para-selectivity is not restored by calcination alone, but that subsequent treatments with TMP can restore such diminished para-selectivity for the toluene disproportionation and ethylation reactions.

EXAMPLE VII

Treatment of Mg-ZSM-5 Damaged by Contamination with Metals and Halogen

An alkylation unit using Example III type Mg-ZSM-5 with two catalyst beds connected in series is used to test catalyst performance for alkylation of toluene with ethylene to produce p-ethyltoluene (PET). Half of the ethylene feed is mixed with the toluene feed leading to the first reactor. The other half is added to the effluent from the first reaction prior to passage through the second bed. Selectivity to PET declined with time. An analysis of the catalyst revealed contamination with metals and chloride as follows:

TABLE IV

| Treatment of Damaged Mg—ZSM-5 with TMP | | | | | | |
|---|---|---|---|---|---|---|
| | New Catalyst | | After Damage in Reactor | | After Treatment with TMP | |
| | Conv. % | Para % | Conv. % | Para % | Conv. % | Para % |
| A. TOL DISPRO. | | | | | | |
| 450° C. | 1.2 | 95.8 | 1.2 | 72.6 | 0.9 | 89.8 |
| 500 | 3.3 | 95.6 | 3.0 | 70.7 | 1.9 | 91.6 |
| 550 | 7.7 | 95.0 | 7.9 | 69.3 | 4.3 | 91.1 |
| 600 | 13.4 | 94.2 | 14.5 | 64.6 | 9.0 | 89.3 |
| B. TOL + $C_2H_4$ | | | | | | |
| 400° C. | 8.0 | 100 | 12.9 | 94.8 | 10.5 | 99.1 |
| 450 | 6.8 | 100 | 10.2 | 92.6 | 8.9 | 98.8 |

The Table IV data demonstrate that trimethylphosphite can be used to reselectivate ZSM-5 type catalysts which have been damaged by metal and halogen contamination.

EXAMPLE VIII

Susceptibility of Organophosphorus Treated Mg-ZSM-5 to Moisture Damage

An Mg-ZSM-5 catalyst of the type prepared in Example III is tested for its conversion and para-selectivity for promotion of ethylation of toluene. The catalyst is then intentionally damaged by introduction of moisture and again tested in toluene ethylation reactions. The catalyst sample is then treated with gaseous trimethylphosphite or gaseous trimethylphosphate and again tested for its activity and para-selectivity in promoting ethylation of toluene. Organophosphorus treated catalyst is then again subjected to moisture treatment and again tested for its toluene ethylation performance. In this manner, the effect of organophosphorus treatment on catalyst moisture susceptibility is demonstrated.

Reaction conditions and conversion and selectivity performance for this testing is set forth in Tables V and VI.

TABLE V

Use of TMP[1] to Regenerate Damaged Alkylation Catalyst[2] And to Reduce Susceptibility to Moisture

| Conditions | % Toluene Conversion[3] | % Para Selectivity |
|---|---|---|
| [4]Toluene + $C_2H_4$ | 23.5 | 96.1 |
| [5]$H_2O$ treatment Toluene + $C_2H_4$ | 26.9 | 88.4 |
| [6]TMP treatment Toluene + $C_2H_4$ | 27.4 | 99.2 |
| $H_2O$ Treatment Toluene + $C_2H_4$ | 24.0 | 98.7 |

[1]Trimethylphosphite, $(CH_3O)_3P$
[2]Mg—ZSM-5
[3]Theoretical conversion = 50%
[4]Toluene = 3.4 WHSV, $C_2H_4$ = 0.5 WHSV; Tol: $C_2H_4$ = 2:1; T = 400° C.
[5]$H_2O$ = 6.0 WHSV, $N_2$ co-feed = 2.9 WHSV at 400° C. for 30 min. 30 min $N_2$ purge at 400° C. before and after treatment.
[6]TMP = 3.1 WHSV, $N_2$ co-feed = 2.9 WHSV at 250° C. for 15 min. 1 hour calcination at 500° C. before and after treatment.

TABLE VI

Use of TMPO[1] to Regenerate Damaged Alkylation Catalyst[2] And to Reduce Susceptibility to Moisture

| Conditions | % Toluene Conversion[3] | % Para Selectivity |
|---|---|---|
| [4]Toluene + $C_2H_4$ | 26.6 | 96.3 |
| [5]$H_2O$ treatment Toluene + $C_2H_4$ | 27.3 | 80.8 |
| [6]TMPO treatment Toluene + $C_2H_4$ | 29.2 | 96.3 |
| $H_2O$ Treatment Toluene + $C_2H_4$ | 26.2 | 95.7 |

[1]Trimethylphosphate, $(CH_3O)_3P=O$
[2]Mg—ZSM-5
[3]Theoretical conversion = 50%
[4]Toluene = 3.4 WHSV, $C_2H_4$ = 0.5 WHSV; Tol: $C_2H_4$ = 2:1; T = 400° C.
[5]$H_2O$ = 6.0 WHSV, $N_2$ co-feed = 2.9 WHSV at 400° C. for 30 min. 30 min $N_2$ purge at 400° C. before and after treatment.
[6]TMPO = 3.1 WHSV, $N_2$ co-feed = 2.9 WHSV at 250° C. for 15 min. 1 hour calcination at 500° C. before and after treatment.

The ability of both gaseous trimethylphosphite and gaseous trimethylphosphate to reselectivate damaged Mg-ZSM-5 alkylation catalysts is demonstrated by the Table V and VI data. Both samples of the catalyst were subjected to the same moisture damaging conditions. The reason for one sample suffering a greater loss in para-selectivity (80.8% vs. 88.8/4%) is unknown. The sample treated with TMP was reselectivated to a para-selectivity (99.2%) greater than that exhibited by the undamaged catalyst (96.1%). In addition, there was a slight improvement in toluene conversion (27.4% for reselectivated catalyst vs 23.5% for undamaged catalyst). Treatment with TMPO restored the damaged (80.8% para-selectivity) catalyst to its pre-damaged para-selectivity of 96.3%. Although para-selectivity shows a greater improvement after TMP treatment that after TMPO treatment, this may be a result of the fact that the sample used for TMP treatment had not sustained as much damage as the sample used in the TMPO study. Both reselectivated catalyst samples exhibited remarkable resistance to moisture following the treatment. When both catalyst were subjected to a second water treatment, little decrease in para-selectivity was observed. Para-selectivity for the TMP treated catalyst decreased from 99.2% before the second water treatment to 98.7% after the treatment. Para-selectivity for the TMPO treated catalyst decreased from 96.3% to 95.7% after the second water treatment.

EXAMPLE IX

An Mg-ZSM-5 catalyst of the type prepared in Example III is tested for its propensity to adsorb selectivity-damaging chloride from a chloride-contaminated toluene feed during a toluene alkylation reaction. Such a toluene alkylation reaction is run for 24 hours on stream using toluene containing 25 ppm Cl (Toluene WHSV=4.7) and an ethylene alkylating agent (Ethylene WHSV=0.4) at a temperature of 400° C. Chloride adsorption by the untreated catalyst, both before and after calcination for 1 hour at 500° C., during such a reaction is determined. The same catalyst is then tested in a similar manner after the catalyst has been treated with two different organophosphorus reagents, trimethylphosphite (TMP) and dimethylmethylphosphonate (DMMP). Treatment conditions, chloride adsorption results, and catalyst phosphorus content are set forth in Table VII. Chloride adsorption percentages in Table VII represent an average of three determinations.

TABLE VII

Relative Chloride Adsorption by Untreated and Organophosphorus-Treated Mg—ZSM-5 Toluene Alkylation Catalyst

| | | % Cl | | |
|---|---|---|---|---|
| Catalyst | Treating Agent | Before Calcination | After Calcination | % P |
| Mg—ZSM-5 | None | 0.62 | 0.34 | 0.01 |
| Mg—ZSM-5 | TMP[1] | 0.02 | 0.02 | 1.00 |
| Mg—ZSM-5 | DMMP[2] | 0.02 | 0.02 | 1.00 |

[1]TMP = 15 ml/hr with $N_2$ Co-Feed at 100 cc per minute - Treatment time is 15 minutes at 200° C.
[2]DMMP = 4.3 ml/hr with $N_2$ Co-Feed at 200 cc per minute - Treatment time is 30 minutes at 150° C.

The Table VII data demonstrate that catalyst treatment with either TMP or DMMP can significantly reduce the tendency of an Mg-ZSM-5 alkylation catalyst to adsorb selectivity-damaging chloride from chloride-contaminated toluene during a toluene alkylation reaction.

What is claimed is:

1. A process for conversion of aromatic compounds to a dialkyl benzene compound mixture enriched in the paradialkylbenzene isomer, said process comprising contacting said aromatic compounds with an alkylating agent under conversion conditions with a catalyst comprising both a crystalline zeolite material having a constraint index within the approximate range of 1 to 12 and a silica/alumina mole ratio of at least 12 and a minor proportion of one or more difficultly reducible oxides, said catalyst being prepared by a method comprising contacting said catalyst with a vapor phase organophosphorus reagent selected from $C_{1-4}$ alkyl phosphite esters, $C_{1-4}$ alkyl phosphate esters and dimethylmethylphosphonate, at a temperature of 100° C. to 300 ° C. and for a period of time and under conditions sufficient to either enhance para-selectivity of said catalyst or to reduce the susceptibility of said catalyst to deselectivation by contact with moisture or halogen.

2. A process according to claim 1 wherein said aromatic compounds comprise toluene and said alkylating agent contains from 1 to about 16 carbon atoms and is selected from olefins and alkyl halides.

3. A process according to claim 1 wherein said difficultly reducible oxide is selected from magnesium oxide, calcium oxide, phosphorus oxide, combinations of magnesium oxide and phosphorus oxide and combinations of calcium oxide and phosphorus oxide.

4. A process according to claim 1 wherein contact between catalyst and organophosphorus reagent occurs at a temperature of from about 150° C. to 250° C., wherein organophosphorus reagent is contacted with catalyst for a period of from about 0.2 to 1.0 hour; and wherein catalyst is contacted with at least about 0.5 gram of organophosphorus reagent per gram of catalyst per hour.

5. A process according to claim 1 wherein said catalyst is contacted with organophosphorus reagent admixed with an inert gaseous diluent selected from nitrogen, carbon dioxide and helium.

6. A process according to claim 1 wherein said zeolite is selected from ZSM-5, ZSM-11, ZSM-12, ZSM-23, ZSM-35, ZSM-38 and ZSM-48.

7. A process according to claim 1 wherein the organophosphorus reagent is trimethylphosphite, tributylphosphite, trimethylphosphate, tributylphosphate, or dimethylmethylphosphonate.

8. A process according to claim 1 wherein said catalyst comprises from about 1 to 99% by weight of zeolite material with the balance of said composition comprising a binder for said zeolite material.

* * * * *